(12) United States Patent
Hari et al.

(10) Patent No.: US 10,946,307 B2
(45) Date of Patent: *Mar. 16, 2021

(54) EXTRACTION OF CANNABINOIDS, CURCUMINOIDS AND GINSENOSIDES

(71) Applicant: Bright Green Corporation, Wilmington, DE (US)

(72) Inventors: V. Hari, Orlando, FL (US); John Stockwell, Leamington (CA)

(73) Assignee: BRIGHT GREEN CORPORATION

( * ) Notice: Subject to any disclaimer, the term of this patent is extended or adjusted under 35 U.S.C. 154(b) by 0 days.

This patent is subject to a terminal disclaimer.

(21) Appl. No.: 16/510,206

(22) Filed: Jul. 12, 2019

(65) Prior Publication Data

US 2020/0016508 A1 Jan. 16, 2020

Related U.S. Application Data

(60) Provisional application No. 62/696,924, filed on Jul. 12, 2018.

(51) Int. Cl.
*B01D 11/02* (2006.01)
*C07C 45/79* (2006.01)
(Continued)

(52) U.S. Cl.
CPC ...... *B01D 11/0288* (2013.01); *B01D 11/0292* (2013.01); *B01D 11/0403* (2013.01);
(Continued)

(58) Field of Classification Search
CPC ............ B01D 11/0288; B01D 11/0203; B01D 39/06; B01D 3/10; B01D 15/08; B01D 11/0211; B01D 1/00; B01D 9/00; B01D 9/0018; B01D 9/0059; B01D 11/0261; B01D 11/028; B01D 15/12; B01D 15/125; B01D 36/00; B01D 36/02; B01D 39/2055;
(Continued)

(56) References Cited

U.S. PATENT DOCUMENTS 8,445,034 B1 * 5/2013 Coles, Jr. ............. A61K 31/192
424/725
9,044,390 B1 * 6/2015 Speier .................... A61K 36/00
(Continued)

OTHER PUBLICATIONS

Munish Puri et al, "Enzyme-assisted extraction of bioactives from plants.", published in "Trends in Biotechnology", vol. 30, Issue No. 1, Jan. 2012. (Year: 2012).*

*Primary Examiner* — Joseph W Drodge
(74) *Attorney, Agent, or Firm* — Carlson, Gaskey & Olds, P.C.

(57) ABSTRACT

An example method for extracting phytochemical oil from plant parts includes freezing plant parts from at least one of *Cannabis sativa, Curcuma longa, Panax ginseng*, and *Panax quinquefolius*. The frozen plant parts are reduced to a plant powder, which is suspended in an aqueous buffer. The aqueous buffer containing the suspended plant powder is incubated with at least one pectinase and at least one cellulase. An aqueous phase of the incubated aqueous buffer is evaporated through steam heating to obtain a steam dried product. Phytochemical oil, which includes at least one of cannabinoids, curcuminoids, and ginsenosides, is extracted from the steam dried product.

20 Claims, 1 Drawing Sheet

(51) Int. Cl.

| | |
|---|---|
| *C07D 311/78* | (2006.01) |
| *C07C 37/82* | (2006.01) |
| *H01J 49/00* | (2006.01) |
| *B01D 11/04* | (2006.01) |
| *C07C 17/00* | (2006.01) |
| *B01D 15/08* | (2006.01) |
| *C07J 17/00* | (2006.01) |

(52) U.S. Cl.
CPC ............ *B01D 15/08* (2013.01); *C07C 37/82* (2013.01); *C07C 45/79* (2013.01); *C07D 311/78* (2013.01); *C07J 17/005* (2013.01); *H01J 49/0027* (2013.01)

(58) Field of Classification Search
CPC ............ B01D 39/2058; B01D 11/0292; B01D 11/0403; A61L 2202/21; A61L 2/005; A61L 2/0011; A61L 2/0017; A61L 2/0047; A61L 2/0064; A61L 2/02; A61L 2/022; A61L 2/10; A61L 2/12; A61L 2/202; C12N 11/18; C11B 1/02; C11B 1/025; C11B 1/04; C11B 1/10; C11B 1/104; C11B 1/108; C11B 3/00; C11B 3/001; C11B 3/003; C11B 3/005; C11B 3/006; C11B 3/008; C11B 3/08; C11B 3/12; C11B 3/16; A61K 36/00; A61K 36/16; A61K 36/185; A61K 36/268; A61K 36/53; A61K 36/532; A61K 36/62; A61K 36/896; A61K 36/906; A61K 36/9066; C07C 45/79; C07C 37/82; C07C 2601/16; C07C 37/004; C07C 39/23; C07C 45/78; C07C 45/81; C07C 45/82; C07C 45/85; C07C 49/248; C07C 49/255; C07D 311/78; H01J 49/0027; C07J 17/005; F26B 5/06

USPC ............ 210/634, 638, 748.1, 760, 770, 774; 424/725, 728, 752, 756, 764, 773, 774, 424/778; 554/8, 20, 21, 22, 175, 206; 435/132, 175, 267, 271

See application file for complete search history.

(56) References Cited

U.S. PATENT DOCUMENTS

| | | | |
|---|---|---|---|
| 9,956,498 B1* | 5/2018 | Tucker | B01D 3/36 |
| 10,557,105 B1* | 2/2020 | Tran | C11B 1/104 |
| 10,675,264 B2* | 6/2020 | Green | A61K 31/045 |
| 2013/0203849 A1* | 8/2013 | Ben Yehuda | A23L 19/105 |
| | | | 514/557 |
| 2013/0280320 A1* | 10/2013 | Mompon | A61K 8/9728 |
| | | | 424/443 |
| 2016/0228385 A1* | 8/2016 | Sievers | A61P 25/36 |
| 2016/0279073 A1* | 9/2016 | Donsky | A61K 47/36 |
| 2017/0266153 A1* | 9/2017 | Levy | A61K 31/352 |
| 2018/0153196 A1* | 6/2018 | Rao | A23L 5/23 |
| 2018/0184705 A1* | 7/2018 | Wasserman | A24B 15/167 |
| 2018/0296616 A1* | 10/2018 | Rivas | A61K 36/185 |
| 2018/0344785 A1* | 12/2018 | Robertson | A61K 36/185 |
| 2018/0369192 A1* | 12/2018 | Green | A61K 31/352 |
| 2019/0032099 A1* | 1/2019 | Johnston | C12P 19/14 |
| 2019/0083418 A1* | 3/2019 | Guy | A61K 31/352 |
| 2019/0192993 A1* | 6/2019 | Levy | B01D 11/0265 |
| 2019/0246591 A1* | 8/2019 | Leo | A01K 67/033 |
| 2020/0061136 A1* | 2/2020 | Venturini Del Greco | A61K 31/352 |

* cited by examiner

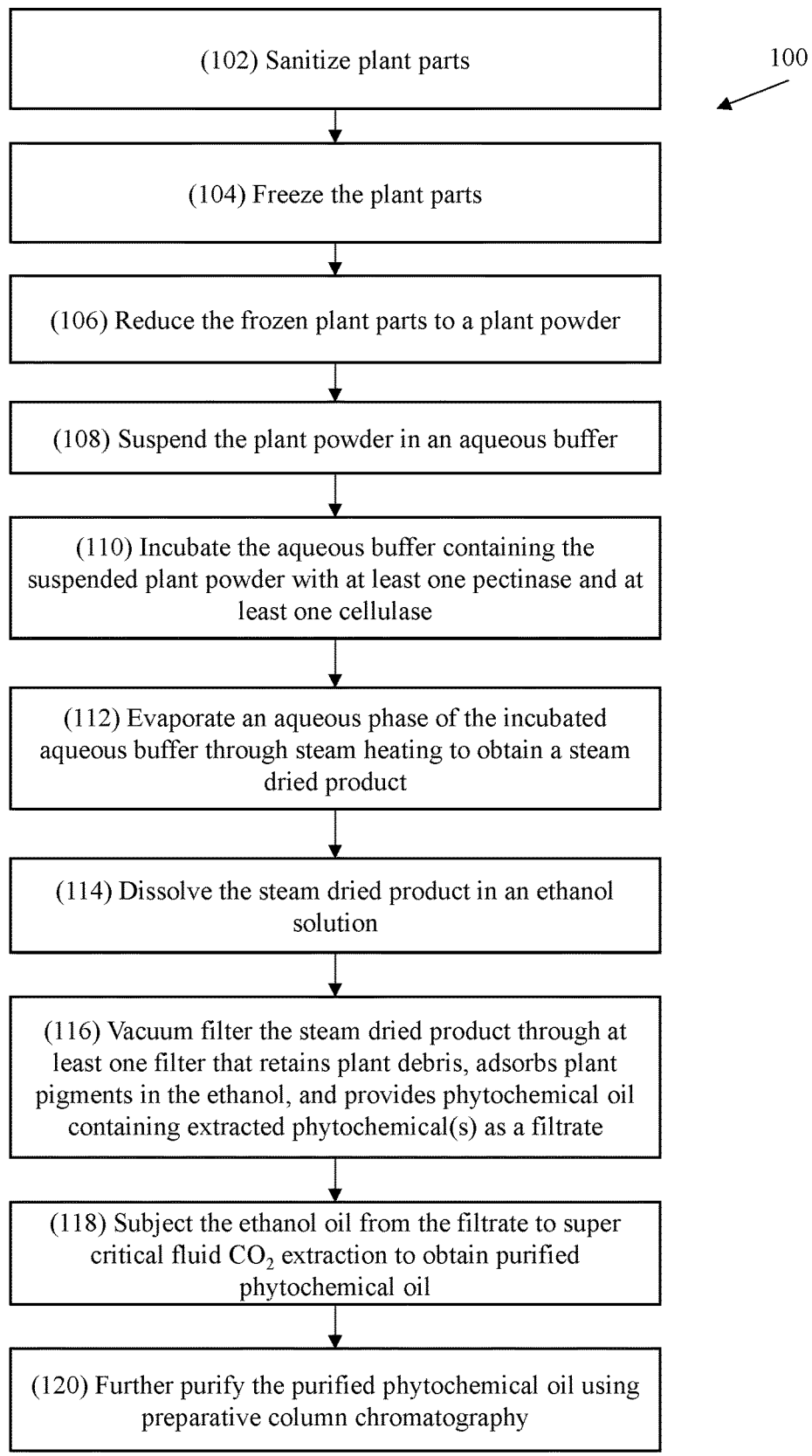

EXTRACTION OF CANNABINOIDS, CURCUMINOIDS AND GINSENOSIDES

CROSS-REFERENCE TO RELATED APPLICATIONS

This application claims priority to U.S. Provisional Application No. 62/696,924, which was filed on Jul. 12, 2018, and is incorporated herein by reference.

BACKGROUND

The present disclosure relates to chemical extraction, and more particularly to a method for extraction of Cannabinoids, Curcuminoids and Ginsenosides.

Cannabinoids are found mainly in the Trichomes of *Cannabis sativa*. Curcuminoids are found mainly in the rhizomes of *Curcuma longa*. Ginsenosides are found in the roots and root hairs of *P. ginseng* and *P. quinquefolius*.

SUMMARY

An example method for extracting phytochemical oil from plant parts includes freezing plant parts from at least one of *Cannabis sativa, Curcuma longa, Panax ginseng*, and *Panax quinquefolius*. The frozen plant parts are reduced to a plant powder, which is suspended in an aqueous buffer. The aqueous buffer containing the suspended plant powder is incubated with at least one pectinase and at least one cellulase. An aqueous phase of the incubated aqueous buffer is evaporated through steam heating to obtain a steam dried product. Phytochemical oil, which includes at least one of cannabinoids, curcuminoids, and ginsenosides, is extracted from the steam dried product.

The embodiments, examples, and alternatives of the preceding paragraph, the claims, or the following description and drawings, including any of their various aspects or respective individual features, may be taken independently or in any combination. Features described in connection with one embodiment are applicable to all embodiments, unless such features are incompatible.

BRIEF DESCRIPTION OF THE DRAWINGS

FIG. 1 is a flowchart depicting an example method of extracting phytochemical oil from plant parts.

DETAILED DESCRIPTION

Cannabinoids, Curcuminoids and Ginsenosides are phytochemicals that are grouped as Adaptogens with multiple pharmaceutical applications as per ethno pharmacology. According to the World Health Organization (WHO), a medicinal plant is any plant which, in one or more of its organs, contains substances that can be used for therapeutic purposes, or which are precursors for chemo-pharmaceutical semi-synthesis. Such a plant contains chemical components that are medically active and its parts including leaves, roots, rhizomes, stems, barks, flowers, fruits, grains or seeds, may be useful if employed in the control or treatment of a disease or condition. For example, Cannabis oil from *Cannabis sativa* contains about 500 different chemical constituents, including the psychoactive tetrahydrocannabinol (THC), non-psychotic Cannabidiol, (CBD) and at least 113 other minor cannabinoids, as well as terpenes and sesquiterpene. THC and CBD alone, or together with other cannabinoids from *Cannabis sativa*, are useful in the treatment of multiple syndromes.

The turmeric plant *Curcuma longa* contains many chemicals collectively called Curcuminoids, which include curcumin (diferuloylmethane), demethoxycurcumin, and bisdemethoxycurcumin as well as many volatile oils. Turmeric-Curcuminoids can serve as an anti-inflammatory agent, immune-modulator and adaptogen in traditional and alternative medicine for treatment of a variety of medical conditions.

Ginseng root powders as well as oil obtained from *Panax ginseng* (Asian Ginseng) or *P. quinquefolius* (American ginseng) can also be prescribed for treating various health related conditions including immunomodulation, stress, mental depression, trauma, erectile dysfunction and other conditions, either for prevention or treatment. Many other herbal products can be similarly prescribed as alternative medicinals.

FIG. 1 is a flowchart depicting an example method 100 of extracting phytochemical oil from plant parts, such as those discussed above. The method 100 is efficient, cost effective, chemically stable, non-toxic and organic. The oil extracted according to the method 100 contains at least one of one or more cannabinoids, one or more curcuminoids, one or more ginsenosides and other biologically active compounds.

In one example, the method 100 involves super-cooling plant parts, powdering the plant parts, enzymatic hydrolysis of cell walls, release of the active medicinals, extraction with ethanol, and removal of plant debris. The multi-step process described here takes advantage of the biology and chemistry of plants.

Medicinally important fresh plants are sanitized (step 102), which may include any one or combination of washing, cleaning, and disinfecting the plants. The disinfecting could include applying UV radiation and/or ozonolysis, for example.

The plants from which the plant parts are obtained in one example include one or more of *Cannabis sativa, Curcuma longa, Panax ginseng*, and *Panax quinquefolius*. Once cleaned and disinfected, extraneous materials and microorganisms are removed from the plant material.

Plant parts from the fresh plants are frozen (step 104). Optionally, this may include chopping the plants into pieces and bagging those pieces. In one example, the freezing is performed at approximately $-80°$ C. (step 104). The freezing can be performed using dry ice, for example. The frozen pieces are powdered or pulverized in the presence of dry ice (e.g., frozen $CO_2$) (step 106). In some examples, the plant pieces are dried and then pulverized and powdered.

The powdered material is then suspended in an aqueous buffer (step 108). In one example, this includes incubating the aqueous buffer at approximately $37°$ C. with approximately 1 mg/ml of pectinases and cellulases for 1-24 hours, depending on the amount of plant material being extracted (step 110). Containers of the suspended plant material can be placed on a shaker platform and gently shaken to distribute the contents, thereby allowing the plant cell walls to be digested, and releasing the contents into the aqueous media.

The contents of the containers are heated, such as by steam heat, to evaporate the aqueous phase, leaving the solids and oil behind as a steam dried product (step 112). Steam heat is beneficial because it also decarboxylates the cannabinoids and thus THC-A, CBD-A and CBN-A are converted respectively into THC, CBD and CBN.

The steam dried product is dissolved in an ethanol solution (step 114), which in one example is 100% pure ethanol.

The volume of ethanol that is provided is sufficient to dissolve the steam dried product. The ethanol solution is vigorously blended so as to extract all the biological material. The extracted material is then vacuum filtered through one or more filters (step 116), such as a charcoal filter, that retains plant debris, adsorbs the plant pigments in the ethanol, and allows the ethanol solvent containing the phytochemicals in oil form to flow through so that the filtrate contains all the extracted phytochemicals.

The ethanol-oil from the filtrate is subjected to super critical fluid $CO_2$ extraction so as to respectively obtain at least one of clean, uncontaminated Cannabis oil, turmeric oil and ginseng oil, depending on which plants were selected to be included in the process (step 118). For example, *Cannabis sativa* is useful for obtaining Cannabis oil, *Curcuma longa* is useful for obtaining turmeric oil, and *Panax ginseng* or *P. quinquefolius* are good sources of ginseng oil. Various sub-species, varieties, hybrids, bio-types, and eco-types of the example plants are useful in different example embodiments of the disclosed method.

In one example, the $CO_2$ purified oils are further purified into their respective components by preparative column chromatography (step 120).

While example plants and oils are mentioned above, the disclosed can also be potentially applied to the extraction of ethno pharmaceuticals from other medicinal plants.

The obtained, respective oils are analyzed for content by gas and gas-mass spectrometric analysis in an example embodiment.

Although example embodiments have been disclosed, a worker of ordinary skill in this art would recognize that certain modifications would come within the scope of this disclosure. For that reason, the following claims should be studied to determine the scope and content of this disclosure.

What is claimed is:

1. A method for extracting phytochemical oil from plant parts, comprising:
    freezing plant parts from at least one of *Cannabis sativa, Curcuma longa, Panax ginseng*, and *Panax quinquefolius;*
    reducing the frozen plant parts to a plant powder;
    suspending the plant powder in an aqueous buffer;
    incubating the aqueous buffer containing the suspended plant powder with at least one pectinase and at least one cellulase;
    evaporating an aqueous phase of the incubated aqueous buffer through steam heating to obtain a steam dried product; and
    extracting phytochemical oil from the steam dried product, the phytochemical oil including at least one of cannabinoids, curcuminoids, and ginsenosides.

2. The method of claim 1, comprising, prior to said freezing:
    sanitizing the plant parts, the sanitizing including at least one of washing, ultraviolet irradiation, and ozonolysis.

3. The method of claim 2, wherein said sanitizing removes microorganisms from the plant parts.

4. The method of claim 3, wherein said reducing the frozen plant parts to a plant powder comprises pulverizing the frozen plant parts.

5. The method of claim 1, wherein:
    said freezing comprises cooling the plant parts with dry ice; and
    said reducing is performed while the plant parts are being cooled by the dry ice.

6. The method of claim 1, wherein said incubating is performed at approximately 37° Celsius.

7. The method of claim 6, wherein the aqueous buffer containing at least one pectinase and at least one cellulase includes approximately 1 mg/ml of said at least one pectinase and at least one cellulase.

8. The method of claim 1, wherein said incubating is performed for 1-24 hours depending on an amount of the plant powder in the aqueous buffer.

9. The method of claim 1, comprising shaking the aqueous solution containing the suspended powder during said suspending to distribute the contents of the aqueous buffer, thereby digesting cell walls of said plant parts, and releasing contents of said plant parts previously contained by the cell walls into the aqueous buffer.

10. The method of claim 1, wherein said evaporating comprises decarboxylating the suspended plant powder.

11. The method of claim 1, wherein said extracting oil comprises:
    dissolving the steam dried product in ethanol to form a solution; and
    blending the ethanol solution that includes the dissolved steam dried product.

12. The method of claim 11, wherein the ethanol is 100% pure.

13. The method of claim 11, comprising:
    vacuum filtering the blended ethanol solution through at least one filter that retains plant debris, adsorbs plant pigments in the ethanol, and provides ethanol oil containing at least one extracted phytochemical as a filtrate.

14. The method of claim 13, wherein the at least one filter includes a charcoal filter.

15. The method of claim 13, comprising:
    subjecting the ethanol oil from the filtrate to super critical fluid $CO_2$ extraction to obtain purified phytochemical oil.

16. The method of claim 15, comprising performing further purifying the purified phytochemical oil using preparative column chromatography.

17. The method of claim 16, wherein the preparative column chromatography comprises high pressure liquid column chromatography.

18. The method of claim 15, comprising:
    analyzing the purified phytochemical oil for cannabinoids, curcuminoids, or ginsenosides using at least one of gas spectrometric analysis and gas-mass spectrometric analysis.

19. The method of claim 1, wherein:
    a portion of the plant parts are obtained from at least one medicinal plant that is not *Cannabis sativa, Curcuma longa, Panax ginseng*, and *Panax quinquefolius*; or
    the phytochemical oil including at least one medicinal compound that is not a cannabinoid, curcuminoid or a ginsenoside.

20. The method of claim 19, wherein said at least one medicinal plant comprises one or more herbs.

* * * * *